United States Patent
Ragbir

(10) Patent No.: US 8,357,204 B2
(45) Date of Patent: Jan. 22, 2013

(54) SET OF MOBILE NECKS FOR INSERTING INTO THE STEM OF A HIP PROSTHESIS

(75) Inventor: Sheila Ragbir, Whim (TT)

(73) Assignee: Adler Ortho S.r.l., Bologna (IT)

( * ) Notice: Subject to any disclaimer, the term of this patent is extended or adjusted under 35 U.S.C. 154(b) by 134 days.

(21) Appl. No.: 12/720,141

(22) Filed: Mar. 9, 2010

(65) Prior Publication Data

US 2011/0125285 A1    May 26, 2011

Related U.S. Application Data

(63) Continuation-in-part of application No. 10/547,150, filed as application No. PCT/IB2004/002874 on Sep. 2, 2004, now abandoned.

(30) Foreign Application Priority Data

Sep. 18, 2003 (CH) ........................... 1599/03

(51) Int. Cl.
    *A61F 2/36* (2006.01)
(52) U.S. Cl. .................................. 623/23.15
(58) Field of Classification Search ..... 623/22.42–22.46
    See application file for complete search history.

(56) References Cited

U.S. PATENT DOCUMENTS

| 4,608,055 A | 8/1986 | Morrey et al. |
| 4,822,370 A * | 4/1989 | Schelhas ................ 623/22.46 |
| 4,963,155 A | 10/1990 | Lazzeri et al. |
| 5,580,352 A | 12/1996 | Sekel |
| 6,299,648 B1 * | 10/2001 | Doubler et al. ............. 623/23.18 |
| 2001/0049561 A1 | 12/2001 | Dews et al. |

FOREIGN PATENT DOCUMENTS

| DE | 36 00 804 | 8/1987 |
| DE | 44 07 227 | 9/1995 |
| EP | 0 201 407 | 11/1986 |
| EP | 0 797 964 | 10/1997 |

* cited by examiner

*Primary Examiner* — David Isabella
*Assistant Examiner* — Ann Schillinger
(74) *Attorney, Agent, or Firm* — Young & Thompson

(57) ABSTRACT

A set of mobile necks for inserting into the stem (2) of a hip prosthesis, in which the mobile necks are produced with different inclinations and lengths in such a way that their free ends (3i), when inserted in the stem, terminate at nine mutually equidistant points (Pi) arranged in three parallel horizontal rows (R0) in such a way that the lines joining the outermost points delineate a square (Q), the length of whose sides is approximately 15 mm, the diagonal (D) of this square coinciding with the axis (H-H) of a mobile neck (1) set at a neutral inclination, that is neither varus nor valgus, with respect to a plane (ss) essentially perpendicular to the axis of the above-mentioned stem (2).

12 Claims, 9 Drawing Sheets

US 8,357,204 B2

SET OF MOBILE NECKS FOR INSERTING INTO THE STEM OF A HIP PROSTHESIS

CROSS REFERENCE TO RELATED APPLICATIONS

This application is a continuation-in-part of application Ser. No. 10/547,150, filed Aug. 26, 2005, which is the 35 U.S.C. §371 national stage of PCT/IB2004/002874, filed Sep. 2, 2004, which claims priority of Swiss application no. 1599/03, filed on Sep. 18, 2003. The entire contents of each of the above-identified applications are hereby incorporated by reference. Any disclaimer that may have occurred during prosecution of the above referenced applications is hereby expressly disclaimed.

BACKGROUND OF THE INVENTION

1. Field of the Invention

The present application relates to the technological sector of the component parts of a hip prosthesis.

2. Description of the Related Art

As is known to those skilled in the art, these component parts consist of a stem, which is fitted into the cavity of the femur, and into this stem is inserted a "neck" (referred to as mobile in the sense that it does not form an integral whole with the said stem), fitted to the free end of which is a spherical head designed to mate with the cavity of the acetabulum.

Mobile necks of the type described above were devised to make it possible, as the need arose, by changing the type of neck used, to create a prosthesis that is anatomically and ergonomically suitable for the skeleton of the patient being fitted with a hip prosthesis.

Mobile necks are therefore produced in sets so that their various dimensions can be used to cover all possible cases. In these sets each neck has a different length and inclination, in such a way that, depending on the physical structure of the patient, the prosthesis is suitable for that structure. In an intervention to fit a hip prosthesis, two important dimensions must be observed: the so-called off-set, which is the distance between the axis of the stem and the centre of rotation of the head, and the height, meaning the distance between a plane perpendicular to the axis of the stem where it connects with the neck, and the abovementioned centre of rotation of the head.

A typical example of the related art is that of Schelhas (U.S. Pat. No. 4,822,370). Schelhas pertains to a hip joint femoral prosthesis having a shaft, a spherical head and connecting part between the shaft and the head. However, Schelhas offers only the possibility of acting on the CCD angle. Thus, the prosthesis of Schelhas allows to position the prosthesis with a certain "tension" of the involved muscles (on the transverse plane) However, if the surgeon rotates (in the recess of the stem of the prosthesis) the neck about its axis to optimize the "tension" of the muscles also varies the position of the center of rotation on the sagittal plane. On the front plane Schelhas does not offer any possibility of variation of the length of the leg of the patient. On the sagittal plane it is possible to vary the stability of the neck but at the same time the "tension" of the involved muscles is also varied. In other words, the angles of antroversion and retroversion in this related art of Schelhas are not independent from one another and the variation of one angle also affects the other angle.

As a consequence, with the sets of mobile necks currently existing on the market, since it is only possible to modify the length or the inclination, the ideal value is obtained for usually only one of these two dimensions, that is either the offset or the height. The reason for this, of course, is that the desired offset can be obtained by for example reducing the length of the mobile neck, but this would simultaneously reduce the height in a way which might not always be acceptable if the intervention is to be successful.

On the other hand there is no question of supplying "made-to-measure" mobile necks in the sense of having the right length and the right inclination relative to the stem, because in the first place the exact measurements can only be found out during the intervention, and in any case the costs would be prohibitive, precluding many people from the chance of undergoing an intervention to fit a hip prosthesis.

SUMMARY OF THE INVENTION

The inventor of the subject of the present application has, in order to avoid all of the drawbacks set out above, devised a set of necks to meet the requirements of all possible hip prosthesis cases. Thus, using in each case one of the necks taken from the said set, it is possible to have hip prosthesis components at ones disposal that are sufficiently adapted to the anatomical structure of the patient, in such a way as to avoid the kind of large imprecisions that can cause sometimes painful post-operative complications that would lead to the intervention being pronounced a failure.

The set of the invention, which makes it possible to obtain the functional advantages described above, is composed of a perfectly acceptable minimum number (15) of necks, all different from each other so as to cover with sufficient precision all possible situations, and can therefore be produced without significantly increasing costs compared with the cost of some present-day sets composed of around ten pieces.

In the first place, as will be seen more clearly below, the 15 mobile necks mentioned above can also cover all the diverse situations of retroversion and anteversion with a single value of off-set in ante/retroversion. In a set of mobile necks according to the invention, the necks are produced with different inclinations and lengths in such a way that their free ends, when inserted in a stem, terminate at nine mutually equidistant points arranged in three parallel horizontal rows, likewise equidistant, in such a way that the lines joining the outermost points delineate a square, the length of whose sides is 15 mm, the diagonal of this square coinciding with the axis of a mobile neck inclined at 45 degree, that is set at a neutral inclination (neither varus nor valgus) with respect to a plane perpendicular to the axis of the abovementioned stem.

The subject of the present invention is therefore a set of mobile necks ($1i$) for inserting into the stem ($2$) of a hip prosthesis, characterized in that the said mobile necks ($1i$) are produced with different inclinations and lengths in such a way that their free ends ($3i$), when inserted in the said stem ($2$), terminate at nine mutually equidistant points ($P_i$) arranged in three parallel horizontal rows ($R_o$) in such a way that the lines joining the outermost points delineate a square (Q), the length of whose sides is approximately 15 mm, the diagonal (D) of this square coinciding with the axis (H-H) of a mobile neck (1) set at a neutral inclination, that is neither varus nor valgus, with respect to a plane ($\beta$) essentially perpendicular to the axis of the abovementioned stem ($2$).

A set of mobile necks for inserting into a stem of a hip prosthesis, where each neck may include a free end configured to be housed in a spherical head, an end distal to the free end configured for insertion into a stem, where a length of the mobile neck, an inclination and an angle of anteversion or retroversion are independent variables, and the free end of each neck, except for three necks, can reach two points by rotating the end distal to the free end by 180°, and where the set comprises fifteen necks and the free ends of said fifteen necks terminate at twenty seven mutually equidistant points arranged in three parallel rows located in three parallel equidistant planes, said two points in a space that said neck can reach being symmetric with respect to a central point of one of the three parallel equidistant planes in which the twenty seven mutually equidistant points may be arranged.

A prosthesis may include a stem, a spherical head, and a mobile neck having a free end configured to be housed in the spherical head and an end distal to the free end configured for insertion into the stem, where a length of the mobile neck, an inclination to the stem and an angle of anteversion or retroversion are independent variables, and the free end of the neck, except for three necks, can reach two points by rotating the end distal to the free end by 180°.

A method for implanting a prosthesis may include inserting a stem into a bone, selecting a mobile neck from a set of mobile necks, the mobile neck having a free end configured to be housed in a spherical head and an end distal to the free end configured for insertion into the stem, and a length of the mobile neck, an inclination to the stem and an angle of anteversion or retroversion are independent variables, and the free end of each neck, except for three necks, can reach two points by rotating the end distal to the free end by 180°.

BRIEF DESCRIPTION OF THE DRAWING FIGURES

Figure 6:
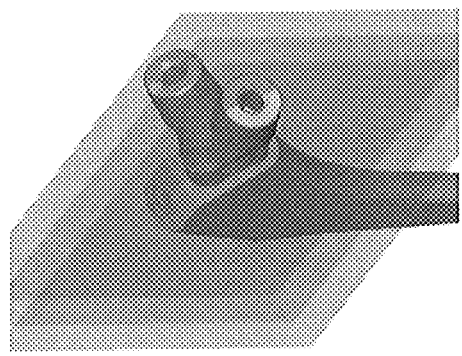
Figure 6:
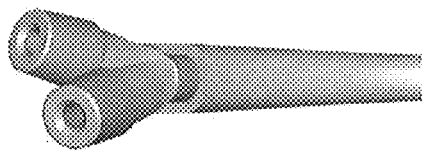
Figure 6:
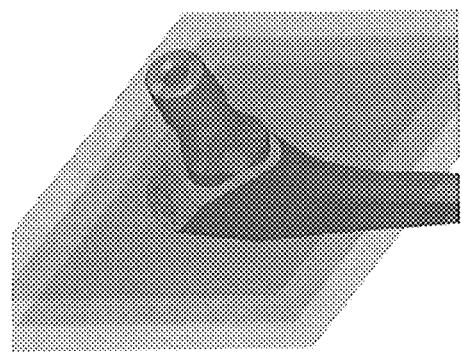
Figure 6:
Figure 6:
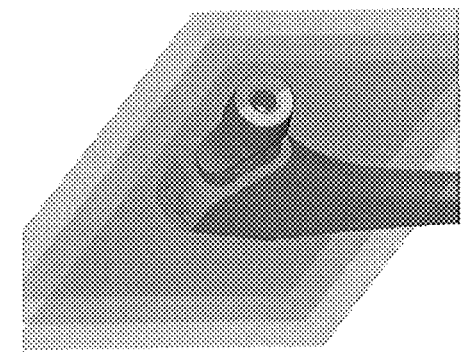
Figure 6:
Figure 7:
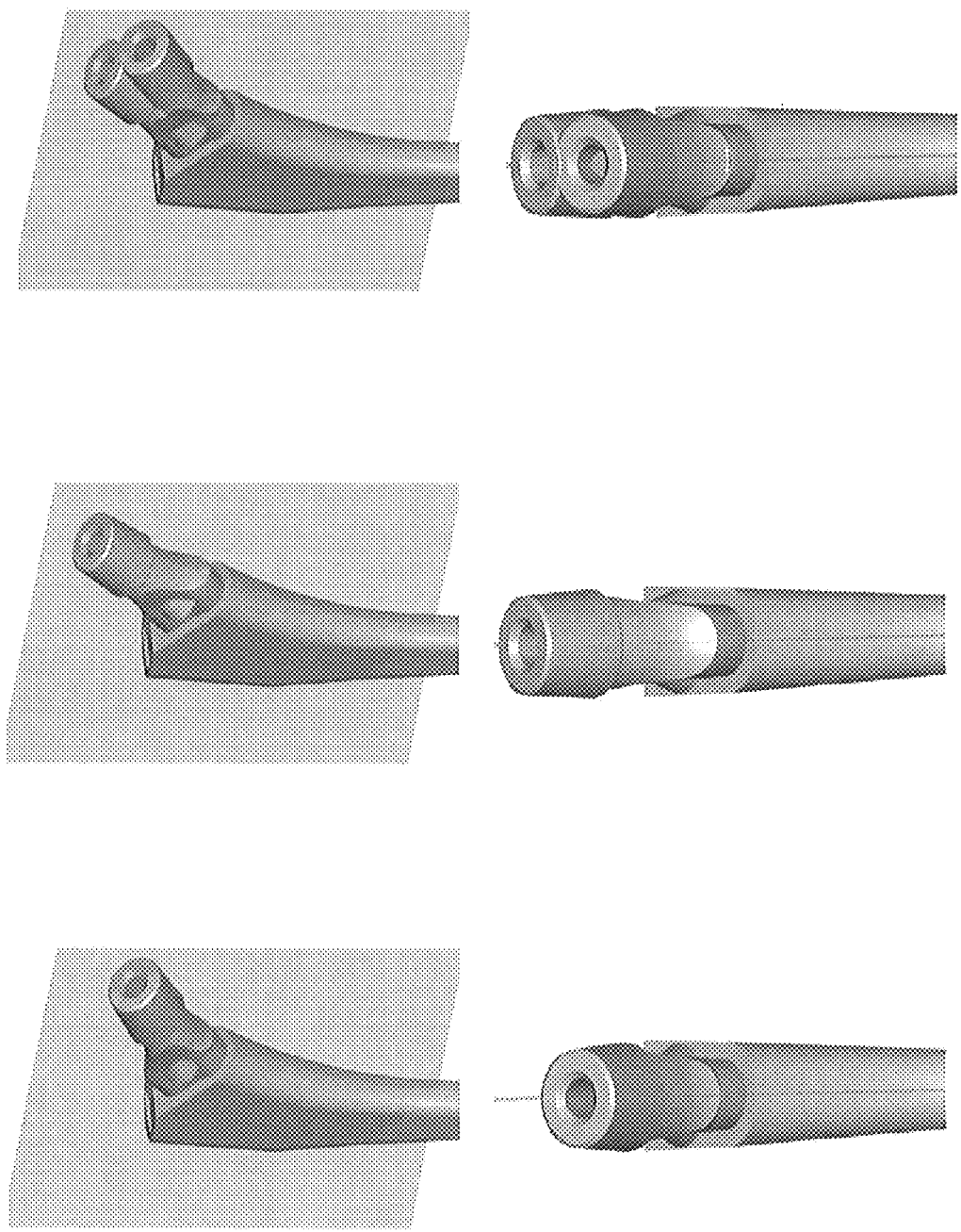
Figure 8:
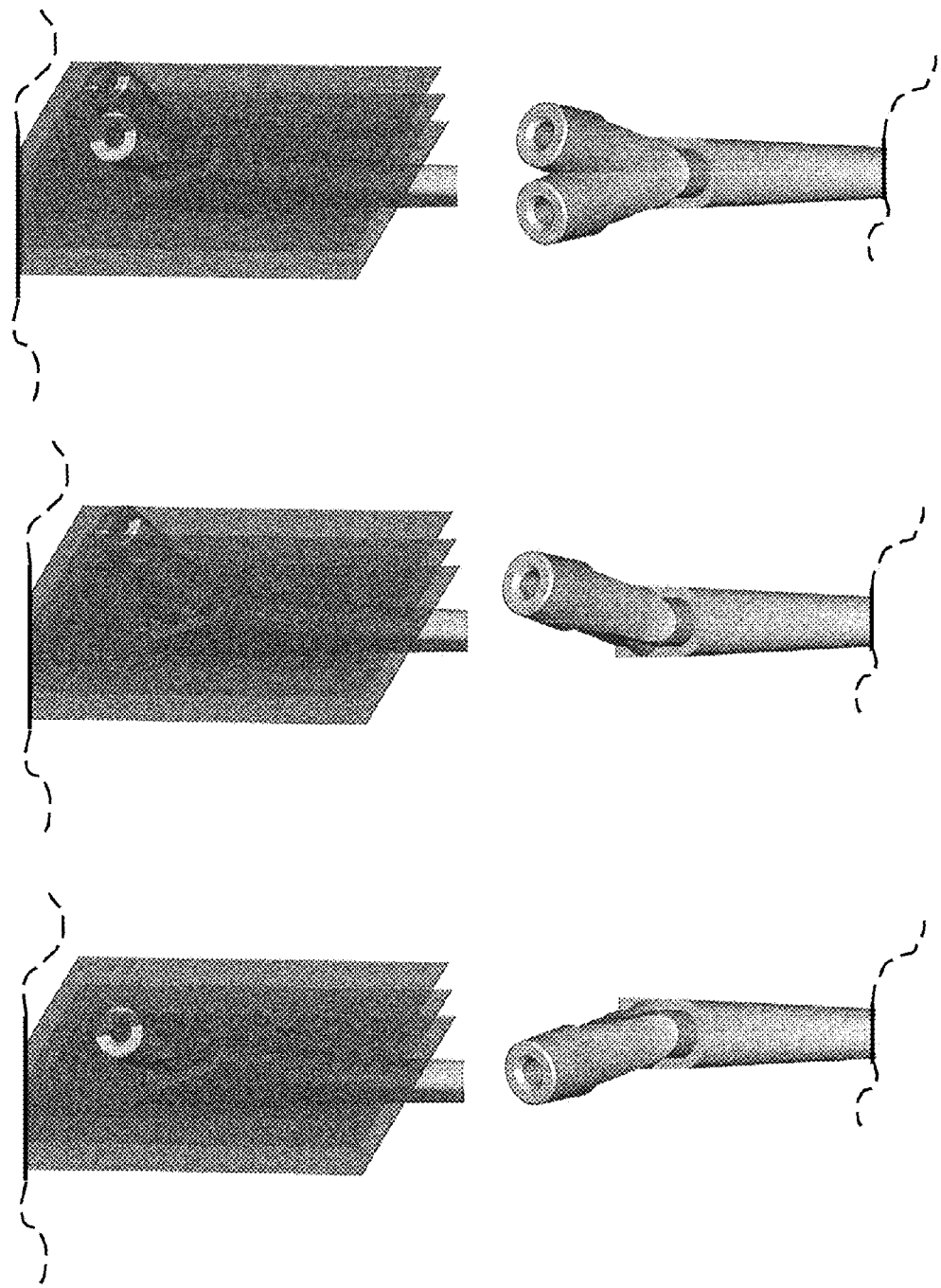
Figure 9:
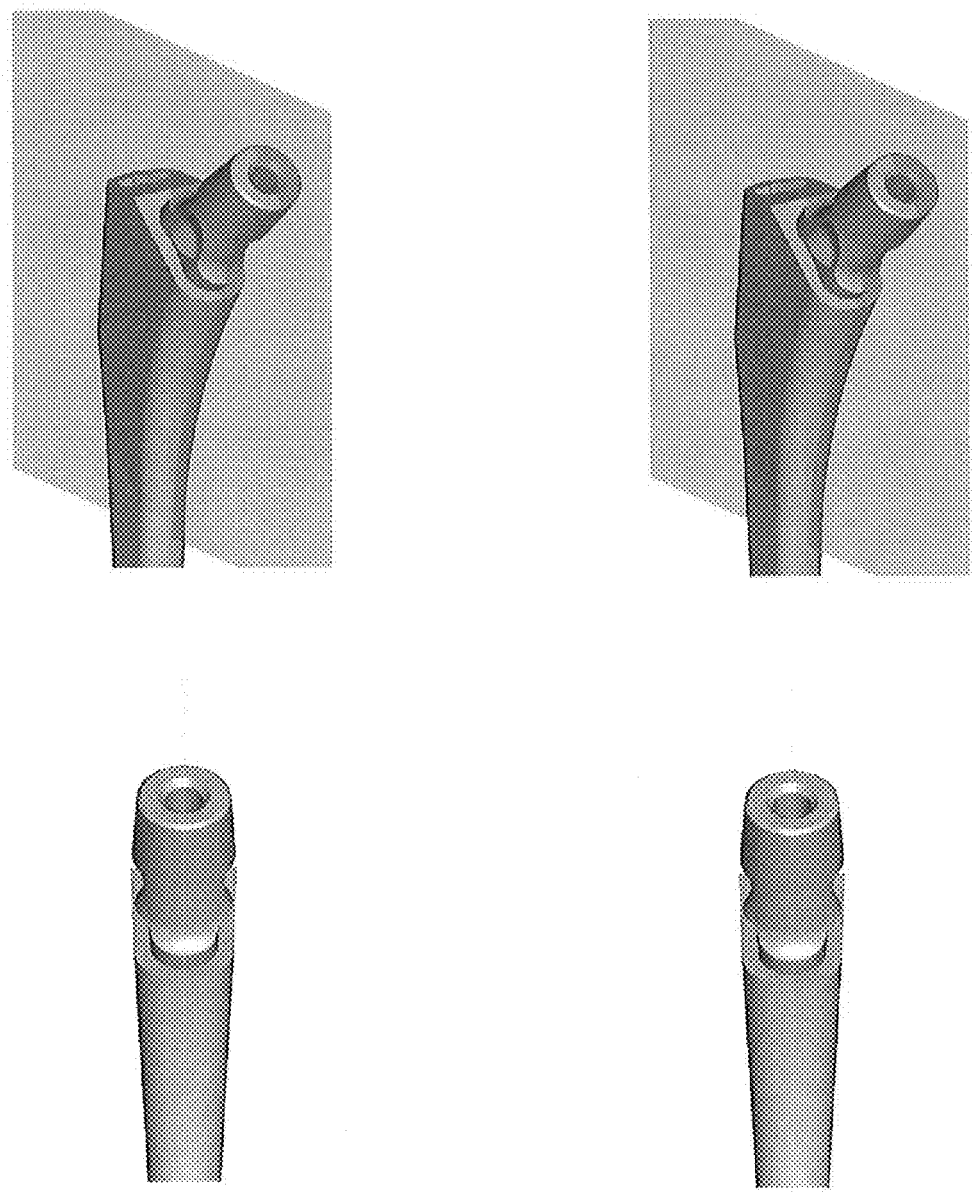

FIG. 6 illustrates possible neck positions.
FIG. 7 illustrates possible neck positions.
FIG. 8 illustrates possible neck positions.
FIG. 9 illustrates possible neck positions.

DETAILED DESCRIPTION OF THE INVENTION

A more detailed description will now be given of an illustrative embodiment of a set according to the invention reference also being made to the accompanying drawing figures.

Figure 1:
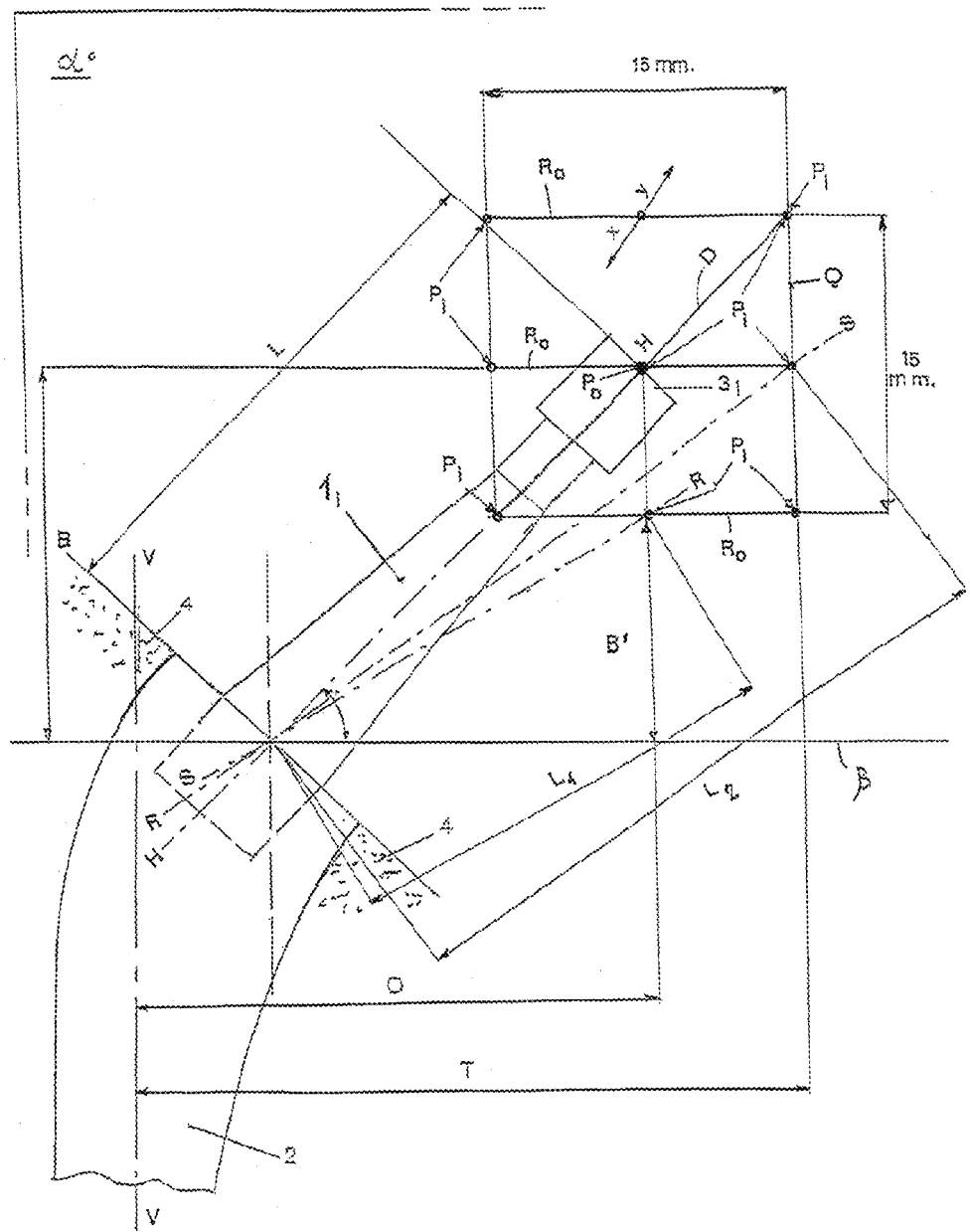
FIG. 1 is an enlarged diagram illustrating the various possible geometrical characteristics of each neck forming a set.
Figure 2:
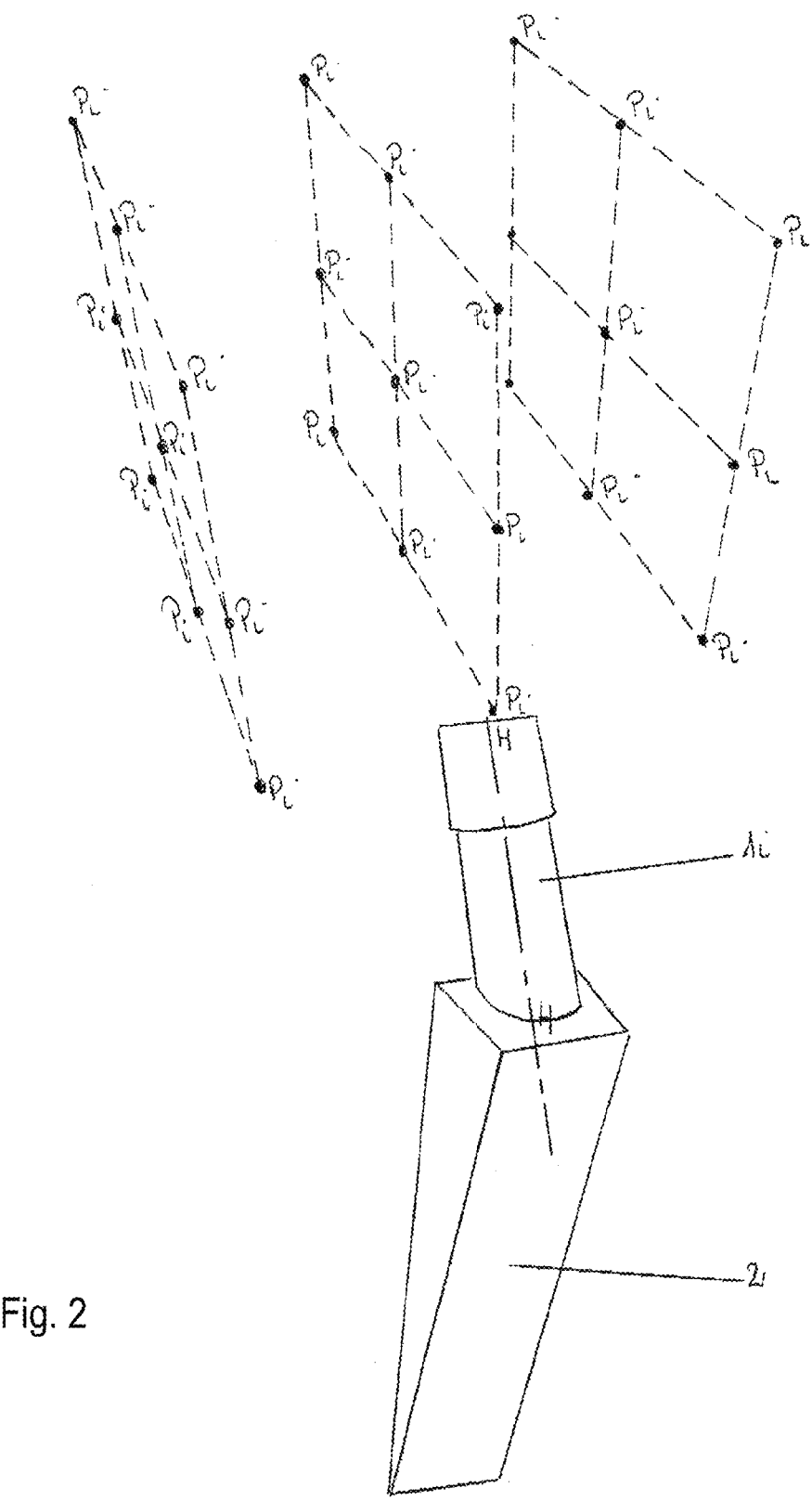
FIG. 2 is a view of the neck orientation.

FIG. 1 is an enlarged diagram illustrating the various possible geometrical characteristics of each neck forming the set. FIG. 2 is another view showing the neck orientation.

Referring to FIGS. 1 and 2, this shows that nine mutually equidistant points $P_i$ are arranged in threes in three horizontal parallel rows $R_o$, which are likewise equidistant from each other.

Part of the stem 2 is inserted into a femur 4, into which there is inserted by known methods one end of a mobile neck 1$i$ belonging to the set of the invention, the free end 3$i$ of which is shaped to allow it to be housed in a spherical head (not shown).

The free end 3$i$ terminates along the axis H-H of the mobile neck at one of the points $P_i$, marked $P_o$ in the drawing figures, and therefore has a length L and an inclination of 45° corresponding to a neutral neck, that is neither varus nor valgus.

This neck 1$i$ (which in the FIGURE terminates as stated at the point $P_o$) gives rise to one particular off-set measurement O and one particular height measurement B. If the anatomical structure of the patient requires the same off-set but a height B' smaller than B, the surgeon simply chooses from the set of mobile necks a neck of length L, of which only the axis R-R is shown with a smaller inclination, and the desired result is obtained.

Similarly, if an off-set O' (that is a distance from the axis V-V of the stem 2) greater than O is required, but the same height B, the surgeon simply selects a mobile neck from among the set of the invention (of which again only the axis S-S is depicted) of length $L_2$, which generates an off-set T greater than O, but which keeps the height B.

The fact that the number of points $P_i$ corresponding to an equivalent number of mobile necks 1$i$ is limited to nine could leave areas in the square Q where none of the mobile necks of the set terminates, but this is overcome by varying in a known manner the type of head fitted, i.e., by varying the depth of the cavity formed inside it to take the end 3$i$ of a mobile neck 1$i$: modifying this depth has the effect (see arrows x, y) of "lengthening" or "shortening" the neck, moving the center of rotation of the head in the two directions, and thus filling the areas described earlier.

It should be pointed out that, on the mobile neck 1$i$ illustrated in full, it is intended that the terminal point of its axis H-H lying on the end 3$i$ should coincide with the centre of rotation of the head that is fitted to this end 3$i$.

As regards how the mobile necks are inclined in anteversion and retroversion, that is with respect to the plane a containing the centers of the articulations of the two legs of the patient, it is sufficient, given the symmetry of the prostheses of limbs, to give the desired different inclinations to a limited number of mobile necks within the set of the invention, with the result already described earlier that as few as 15 mobile necks 1$i$, all different from each other, as stated, can create a set complete enough to be used in practically all cases normally treated. For this purpose the inventor recommends that the distance between the points $P_i$ be approximately 7.5 mm in both directions, so that the square Q enclosing them has a side of length of about 15 mm.

Another note concerns the definition of length (L, $L_1$, $L_2$) of a mobile neck: obviously, this length is the actual axial length of the mobile neck when the inclination of the latter is not corrected in either anteversion or retroversion. In the other cases this length corresponds to the projection onto the above-mentioned plane of the actual length of the mobile neck.

As can be seen in the neck configuration set shown in FIGS. 1 and 2, three necks may be exempt from reaching two points by rotation. With only fifteen necks it is possible to fit any patient. In fact, the fifteen necks of the present application allow to cover all the points in the space, these points being obtained by varying one variable at a time, while keeping the other two variable constant.

This means that in the solution of the present application it is possible to vary the length of the neck while maintaining the inclination and angle of anteversion or retroversion constant. This is true for each one of the three variables.

In the present application each neck can reach two symmetrical points in the space, rotating the neck by 180°.

For example, for a set of fifteen necks, free ends of the fifteen necks may terminate at twenty seven mutually equidistant points arranged in three parallel rows located in three parallel equidistant planes, the two points in a space such that the neck can reach being symmetric with respect to a central point of one of the three parallel equidistant planes in which the twenty seven mutually equidistant points are arranged. Or, if nine necks of are meant to terminate each at one point, thus creating nine points total.

As to the fifteen necks of which three cannot be rotated to reach two points, this is clear in FIGS. 1-5 that the twenty seven points in the space, are arranged on three different and parallel planes.

The geometry of the present invention can be further elucidated in light of FIGS. 3-9.

It should be noted that in order to achieve good results with hip prosthesis, the surgeon has, on the transverse plane, to position the prosthesis so that the muscles that connect the femur to the pelvis are properly "tensioned" (neither too tight nor too loose).

In order to achieve the above, it is necessary that the "offset", that is, the distance between the axis of the femur and the (parallel) axis of the femur head is optimum.

On the front plane the surgeon has to position the prosthesis so that the length of the limb after the surgery is the correct one. In other words, the length of the leg has to be the correct one without altering the tension of the muscles that had been previously determined.

On the sagittal plane, the surgeon has to position the prosthesis so that it is stable.

Figure 3:
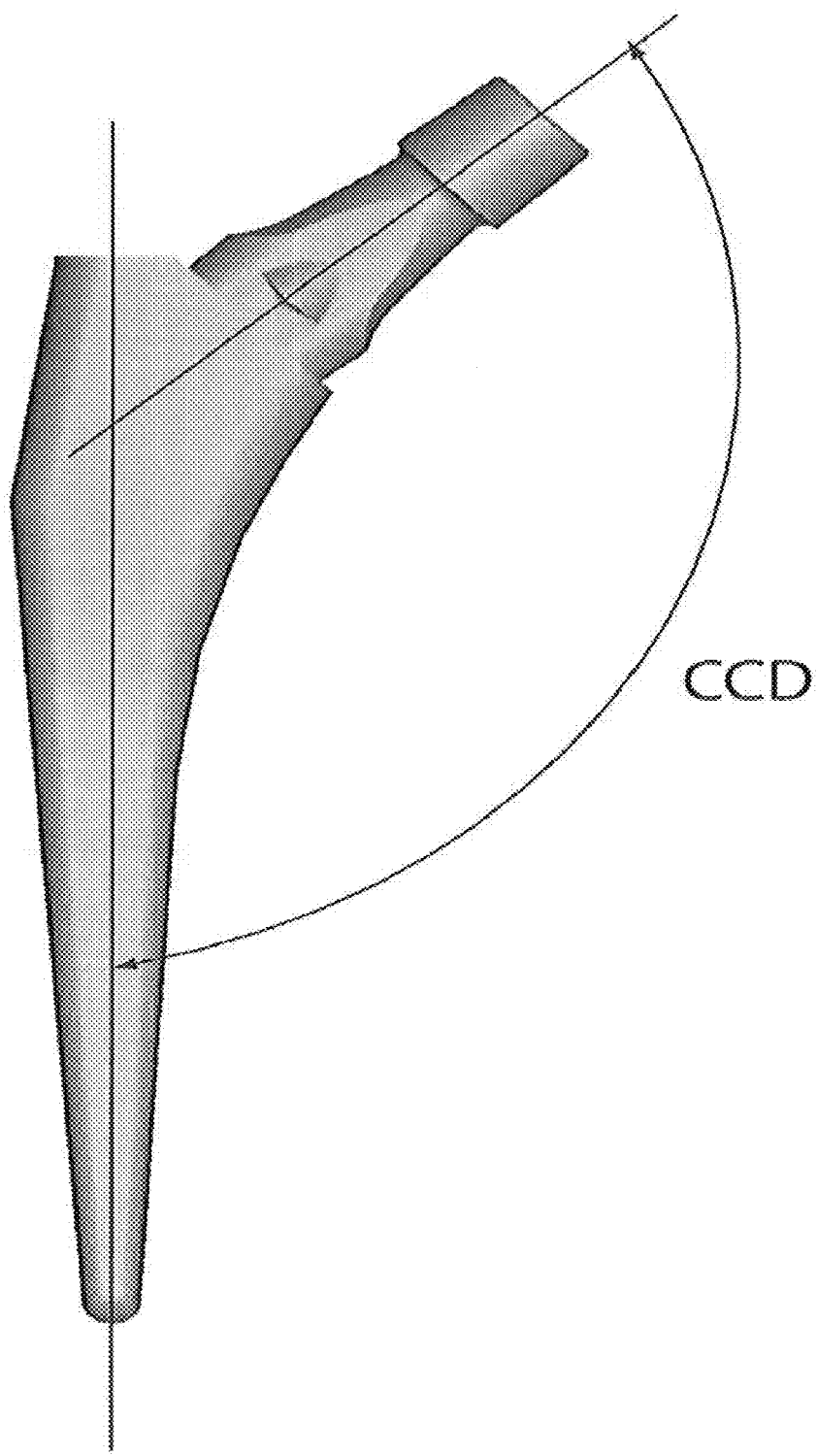
FIG. 3 illustrates the CCD angle between the axis of the femur and the axis of the femur neck.

In anatomy, a so-called CCD angle is defined, as illustrated in FIG. 3, which is the angle between the axis of the femur and the axis of the femur neck.

Figure 4:
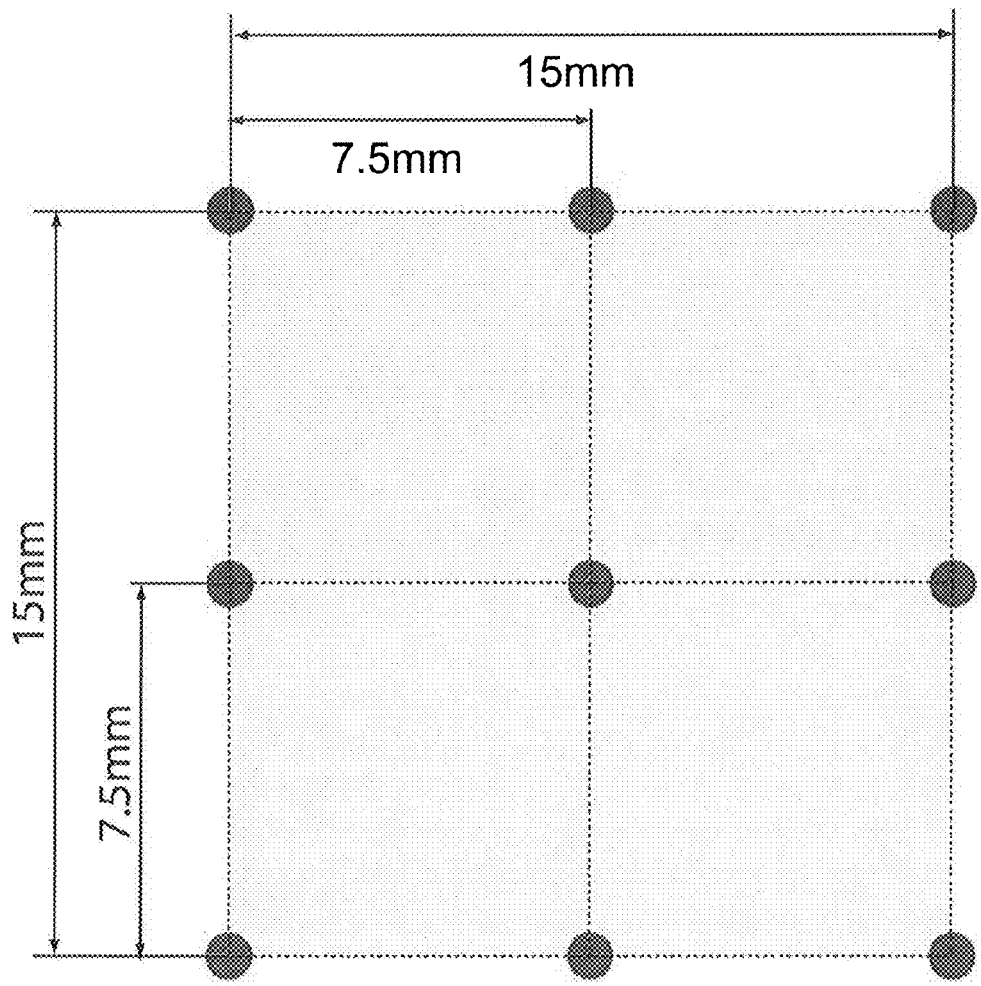
FIG. 4 illustrates a bidimensional matrix with 3×3 positions.

As stated the above, and with reference to attached FIGS. 4 and 5, it is observed as follows:

In the present application, there are three square matrices, each bi-dimensional matrix represents nine positions arranged in column of 3×3 positions.

Figure 5:
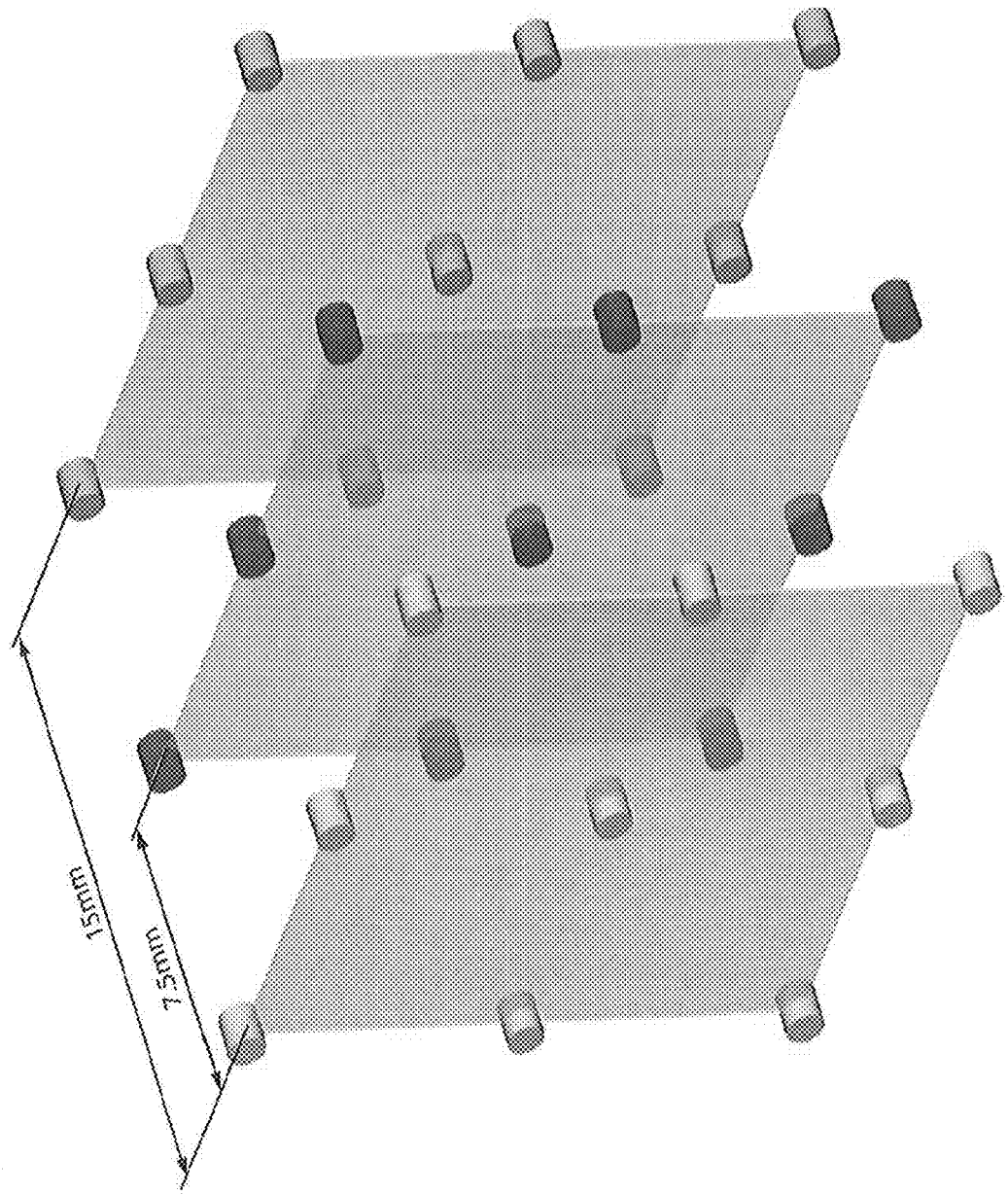
FIG. 5 illustrates a column of bidimensional matrices with 3×3 positions.

As illustrated in FIG. 5, the three matrices, when arranged one parallel to the other, define a "cube" that is a three-dimensional figure.

Looking from the front plane (first matrix of FIG. 5), one will see 9 points, three on each row having the same height. Thus, each row of the matrix defines three points having the same height, while each column of the matrix defines three points having the same offset.

Behind the first matrix there are other two matrices (see FIG. 5) whose points have the same values for height and offset, but different as far as the sagittal plane is concerned.

Therefore, 27 points in the space are defined. However, in order to reach those 27 points in the space only 15 necks are needed. In fact, 12 necks (that do not have the axis in line with the axis of the neck of the prosthesis) properly rotated by 180°, occupy two positions each in the space, and thus 24 points of the space are reached.

Finally, 3 necks (that have the axis in line with the axis of the neck of the prosthesis) even if rotated by 180°, do no change their position in the space.

Thus the total number of necks needed to reach the 27 points in the space is 15 necks.

The possible neck positions are illustrated in FIGS. 6, 7, 8 and 9.

What is claimed is:

1. A set of mobile necks for inserting into a stem of a hip prosthesis, each neck comprising:
   a free end configured to be housed in a spherical head; and
   an end distal to the free end configured for insertion into a stem;
   wherein a length of the mobile neck, an inclination and an angle of anteversion or retroversion are independent variables, and the free end of each neck, except for three necks, can reach two points by rotating the end distal to the free end by 180°,
   and wherein the set is constituted by fifteen necks and the free ends of said fifteen necks terminate at twenty-seven mutually equidistant points arranged in three parallel rows located in three parallel equidistant planes, said two points in a space that said neck can reach being symmetric with respect to a central point of one of the three parallel equidistant planes in which the twenty seven mutually equidistant points are arranged,
   wherein, the free ends of nine necks, of said fifteen necks, terminate at nine mutually equidistant points arranged in three parallel rows for each plane of said three parallel equidistant planes, and
   wherein, said fifteen necks define a set of necks sufficient to fit any patient.

2. The set of mobile necks according to claim 1, wherein for each plane the set comprises nine necks of said fifteen necks.

3. The set of mobile necks according to claim 2, wherein the points delineate a square having a side length of about 15 mm.

4. The set of mobile necks according to claim 3, wherein the set of nine necks are inclined to form the square with a displacement in anteversion or retroversion with respect to a plane containing centers of articulation of two legs of a patient.

5. The set of mobile necks according to claim 1, wherein the axis of three necks have a neutral inclination.

6. A prosthesis, comprising:
   a stem;
   a spherical head; and
   a mobile neck having a free end configured to be housed in the spherical head and an end distal to the free end configured for insertion into the stem,
   wherein a length of the mobile neck, an inclination to the stem and an angle of anteversion or retroversion are independent variables, and the free end of the neck, except for three necks, from a group of necks consisting of fifteen necks, can reach two points by rotating the end distal to the free end by 180°,
   wherein said fifteen necks define a set of necks sufficient to fit any patient,
   free ends of said fifteen necks terminate at twenty-seven mutually equidistant points arranged in three parallel rows located in three parallel equidistant planes, said two points in a space that said neck can reach being symmetric with respect to a central point of one of the three parallel equidistant planes in which the twenty seven mutually equidistant points are arranged, and
   the free ends of nine necks of said fifteen necks, terminate at nine mutually equidistant points arranged in three parallel rows for each plane of said three parallel equidistant planes.

7. The prosthesis according to claim 6, wherein the free ends of a set of nine necks taken from the group of fifteen necks terminate at nine mutually equidistant points arranged in three parallel rows.

8. The prosthesis according to claim 7, wherein the nine mutually equidistant points delineate a square having a side length of about 15 mm.

9. The prosthesis according to claim 8, wherein the set of nine necks are inclined to form the square with a displacement in anteversion or retroversion with respect to a plane containing centers of articulation of two legs of a patient.

10. The set of mobile necks according to claim 6,
    wherein, the free ends of nine necks, of said fifteen necks, terminate at nine mutually equidistant points arranged in three parallel rows for each plane of three parallel equidistant planes.

11. A set of mobile necks (1*i*) for inserting into a stem (2) of a hip prosthesis, consisting of:

fifteen of mobile necks (1*i*) which with different inclinations and lengths such that their free ends (3*i*), when inserted in the stem (2), terminate at at least nine mutually equidistant points (Pi) arranged in three parallel horizontal rows (Ro) such that i) lines joining the outermost points delineate a square (Q), ii) a length of each side of the delineated square is approximately 15 mm, iii) a diagonal (D) of the square coincides with an axis (H-H) of a mobile neck (1) set at a neutral inclination, that is neither varus nor valgus, with respect to a plane (fJ) essentially perpendicular to an axis of the stem (2), wherein, said fifteen necks define a set of necks sufficient to fit any patient.

12. The Set according to claim 11, wherein, in use with a patient, the axes of at least some of the said mobile necks (1*i*) are inclined to form the square (Q) of nine points with a desired displacement of the nine points in anteversion or retroversion with respect to a plane (a) containing centers of the articulations of the two legs of the patient.

* * * * *